United States Patent [19]

Shackle

[11] 3,985,930

[45] Oct. 12, 1976

[54] CYCLOPOLYMETHYLENEFLUORAN COMPOUNDS

[75] Inventor: Dale Richard Shackle, Chillicothe, Ohio

[73] Assignee: The Mead Corporation, Dayton, Ohio

[22] Filed: Mar. 4, 1976

[21] Appl. No.: 663,963

[52] U.S. Cl. ............................... 428/307; 260/335; 282/27.5; 427/151; 428/914
[51] Int. Cl.² .......................................... B41L 1/20
[58] Field of Search ........... 428/307, 914; 282/27.5; 260/335; 427/151

[56] References Cited
UNITED STATES PATENTS

| | | | |
|---|---|---|---|
| 3,506,471 | 4/1970 | Kimura et al. | 428/307 |
| 3,669,710 | 6/1972 | Kimura et al. | 428/307 |
| 3,769,057 | 10/1973 | Lin | 428/307 |

Primary Examiner—William J. Van Balen
Attorney, Agent, or Firm—Wilson G. Palmer

[57] ABSTRACT

Novel fluoran compounds are produced represented by the general formula

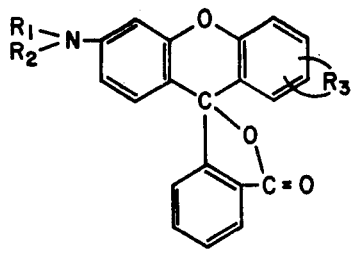

wherein $R_1$ and $R_2$ each represent a lower alkyl group containing one to four carbon atoms and wherein $R_3$ is a cyclopolymethylene group containing from three to four carbon atoms.

In another aspect of the invention, pressure sensitive transfer paper is produced, the transfer paper comprising a substrate having coated thereon pressure rupturable capsules containing an organic solvent solution of the novel substantially colorless cyclopolymethylenefluoran compound of this invention, the organic solvent solution of the substantially colorless cyclopolymethylenefluoran compound being capable of forming a colored dye in contact with an electron-acceptor.

In another aspect of this invention, a process is provided for producing the novel cyclopolymethylenefluoran compound of this invention by reacting equimolar quantities of a 2-(4'-N,N lower alkyl substituted amino-2'hydroxybenzoyl) benzoic acid with a phenol selected from the group consisting of 5-indanol and 5,6,7,8-tetrahydro-1-naphthol for a time period ranging from about 1 to about 24 hours at a temperature ranging from about 35 to about 110° C. in sulfuric acid having a concentration above about 70% and thereafter recovering the reaction product.

6 Claims, No Drawings

CYCLOPOLYMETHYLENEFLUORAN COMPOUNDS

BACKGROUND OF THE INVENTION

The present invention relates to novel cyclopolymethylenefluoran compounds which are colorless or substantially colorless, but are instantaneously colorable when brought into reactive contact with suitably sensitized sheets containing an acidic electron-acceptor such as the protic acids, e.g., organic acids, phenolic acids, phenols, diphenols, phenolic resins of the novolak type, and aprotic acids, e.g., Lewis acids, acid clays, etc., or mixtures of these materials. These properties and others disclosed hereinafter make the compounds of this invention suitable for use in various types of carbonless pressure-sensitive copy papers, thermally-sensitive imaging papers, thermally-sensitive imaging transparencies for overhead projection screens and other copy or image applications.

A number of chemical compounds are disclosed in the prior art to be useful as color-precursors when brought into contact with acidic electron-acceptors. Included in the suitable compounds are the 6-dialkylamino fluoran compounds having alkyl groups in the 1,2 and/or 3 position, the preparation of which and/or use in pressure sensitive transfer papers are disclosed in U.S. Pat. Nos. 3,442,908, issued May 6, 1969 to Michio Orita et al., 3,637,757, issued Jan. 25, 1972 to Chao-Han Lin, 3,641,011, issued Feb. 8, 1972 to Chao-Han Lin et al., and 3,713,863, issued Jan. 30, 1973 to Chao-Han Lin et al. None of these prior art patents disclose fluoran compounds which include a cyclopolymethylene group on the fluoran structure. U.S. Pat. No. 3,901,918, issued Aug. 26, 1975 to Koichi Koga et al., discloses 2-amino fluoran compounds with a tetramethylene group attached to the benzene ring at the 3,4 position.

This application is related to commonly assigned U.S. application Ser. No. 461,860, filed Apr. 18, 1974, now U.S. Pat. No. 3,929,825.

STATEMENT OF THE INVENTION

In one aspect of the invention, novel fluoran compounds are produced represented by the general formula

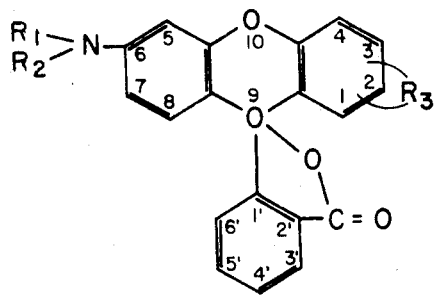

wherein $R_1$ and $R_2$ each represent a lower alkyl group containing one to four carbon atoms and wherein $R_3$ is a cyclopolymethylene group containing three to four carbon atoms.

In another aspect of the invention, pressure-sensitive transfer paper is produced, the transfer paper comprising a substrate having coated thereon pressure rupturable capsules containing an organic solvent solution of the novel substantially colorless cyclopolymethylenefluoran compound of this invention, the organic solvent solution of the substantially colorless cyclopolymethylenefluoran compound being capable of forming a colored dye in contact with an electron-acceptor.

In another aspect of this invention, a process is provided for producing the novel cyclopolymethylenefluoran compound of this invention by reacting equimolar quantities of a 2-(4'-N,N lower alkyl substituted amino-2'hydroxybenzoyl) benzoic acid with a phenol selected from the group consisting of 5-indanol and 5,6,7,8-tetrahydro-1-naphthol for a time period ranging from about 1 to about 24 hours at a temperature ranging from about 35° to about 110° C. in sulfuric acid having a concentration above about 70% and thereafter recovering the reaction product.

DETAILED DESCRIPTION OF THE INVENTION

A preferred process for producing the novel compounds of this invention involves the condensation of equimolar parts of a 2-(4'-N,N low alkyl substituted amino-2'-hydroxybenzoyl) benzoic acid with a phenol having a cyclopolymethylene group of 3 to 4 carbon atoms attached to the benzene ring in the 3 and 4 positions. The general condensation reaction is described in U.S. Pat. No. 3,442,908. In the instant invention, the condensation reaction is as follows

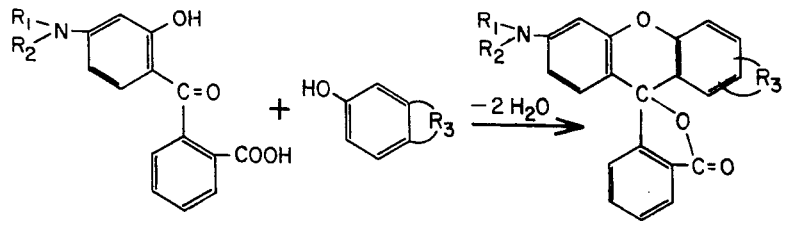

wherein $R_1$ and $R_2$ each individually represents a lower alkyl group containing one to four carbon atoms, $R_3$ is a cyclopolymethylene group containing from three to four carbon atoms.

The above reaction can produce isomers in which the cyclopolymethylene group may be attached to the benzene ring in either the 1,2 or 2,3 positions. These can exist either partially or exclusively. The 2,3 position is preferred since the reaction for the formation of this isomer is less sterically hindered than the reaction to produce the 1,2 isomer. The instant invention is concerned with the products formed by the preferred condensation reaction as heretofore illustrated and to their use in color formation with electron-acceptor materials.

Typical examples of the lower alkyl substituted aminohydroxybenzoyl benzoic acids are:

2-(4'-N,N-dimethylamino-2'-hydroxybenzoyl) benzoic acid, 2-(4'-N,N-diethylamino-2'-hydroxybenzoyl) benzoic acid and 2-(4'-N,N-dibutylamino-2'-hydroxybenzoyl) benzoic acid.

These may be in turn prepared by known processes involving the condensation of phthalic anhydride with a m-dialkylaminophenol. One such process is described in U.S. Pat. No. 3,501,331, issued Mar. 17, 1970 to Shiro Kimura et al.

Typical examples of the phenols having a cyclopolymethylene group are 5-indanol and 5,6,7,8-tetrahydro-1-naphthol.

The preferred conditions under which the condensation reaction can be performed are as follows. Approximately equimolar quantities of an aminohydroxybenzoyl benzoic acid and a phenol containing a cyclopolymethylene group are mixed together in a strongly acid media and heated to a temperature of about 35° C. to about 110° C. for a period of about 1 hour to about 24 hours after which the reaction product is recovered by cooling to room temperature, pouring the mixture into ice water, adjusting the pH to approximately 7 and collecting the solid product on a filter. The product can be further purified by extracting with hot benzene, treating the extract with charcoal and filtering the evaporating the benzene to obtain the solid purified fluoran compound. The acid medium can be, for example, sulfuric acid, phosphoric anhydride or polyphosphoric acid.

Sulfuric acid is the preferred condensation medium because of its low cost, ease of handling and non-volatility, generally yielding clear reaction solutions capable of processing by simply cooling and diluting in ice water and recovering the product in one of several ways. When the acid medium is sulfuric acid, about 70% minimum concentration of the acid can be used. However, a more preferred concentration is about 80% to about 95%. The higher concentrations are more effective in keeping the reactants in solution than the more dilute acids. The more preferred range of time and temperature of reaction is about 2 hours to about 4 hours at about 70° C. to about 95° C.

The fluoran compounds of this invention can be dissolved in organic solvents or oils, such as chlorinated biphenyl, chlorinated biphenyl ether, isopropylbiphenyl, and alkylated naphthalenes. Such solutions of these compounds produce a red color in contact with solid electron-acceptors such as acid clays, organic acids, inorganic acids, phenols and phenolic resins coated on or impregnated in a substrate, such as paper.

The examples which follow illustrate, but do not limit, the preferred embodiments of this invention.

EXAMPLE 1

Preparation of 1,2-(or 2,3-) cyclotrimethylene-6-diethylamino fluoran

Twenty-six and one-tenth grams of 2-(4'-diethylamino-2'-hydroxybenzoyl) benzoic acid, 8.7 g. of 5-indanol and 225 g. of concentrated sulfuric acid were mixed and then heated on an oil bath for 3 hours at 95°–100° C. The mixture was cooled to room temperature and then poured into ice water (about 1200 ml.). The pH was adjusted to 7 with $HN_4OH$. The resulting mixture was filtered and the collected solid was dried. The crude product was then extracted with benzene in a Soxhlet extractor. The benzene solution was then treated with charcoal and filtered. Petroleum ether was added to the benzene solution to crystallize the product. The product had a melting point of 261° C.

Analysis of Product: Calculated: %C, 78.8%, % H, 6.1%; Found: %C, 78.7%, % H, 6.1%.

Solutions of the product in acetone, ethanol, or isopropylbiphenyl gave red colors on paper coated with phenolic novolak resins.

EXAMPLE 2

Preparation of 1,2-(or 2,3-) cyclotetramethylene-6-diethylamino fluoran

Four and one-half grams of 5,6,7,8-tetrahydro-1-naphthol, 8.7 g. of 2-(4'-diethylamino-2'-hydroxybenzoyl) benzoic acid and 75 g. of concentrated sulfuric acid were mixed and then heated on an oil bath for 3 hours at 100° C. The mixture was then allowed to cool to room temperature and then poured into ice water. The pH was adjusted to 7.0 and the resulting solid was collected on a filter. The solid was then extracted in a Soxhlet extractor with benzene. The extract was treated with charcoal and then filtered. Evaporation of the benzene yielded the product. The product has a melting point of 191° C.

Solutions of the product in acetone, ethanol, or isopropylbiphenyl gave red colors on paper coated with phenolic novolak resins.

Pressure-sensitive copy papers are known which use an acid electron-acceptor material on the top surface thereof, and an overlying surface having microcapsules containing a color former in an oil solution, as shown, for example, in U.S. Pat. No. 2,712,507, issued July 5, 1955 to Barrett Green. Alternatively, the acid electron-acceptor material and microcapsules containing the oil solution of the color former can be intermixed and applied to the surface of a substrate such as paper or the like.

Application of pressure, as by a typewriter key, ruptures the microcapsules, causing the color former-oil solution to contact the acid electron-acceptor material, resulting in color formation. In the case where the acid electron-acceptor material and the microcapsules containing the oil solution of the color former are on separate surfaces, it is necessary that the surfaces be in contact during the application of pressure to permit the transfer of the color former-oil solution from ruptured microcapsules to the acid electron-acceptor material. Examples of suitable acid electron-acceptor materials have been given supra.

Oil solutions of the cyclopolymethylenefluoran compounds of this invention, either alone or with other color formers, can readily be encapsulated by a variety of methods, as for example, the method described in U.S. Pat. Nos. 2,800,457, issued July 23, 1957 to Barrett Green et al. and 3,796,669, issued Mar. 4, 1974 to Masataka Kiritani et al. When used alone, the compounds of this invention produce intense red colors. When used in suitable admixture with blue- and orange-producing color formers, or with blue- and green-producing color formers, deep blue or blue-black colors are produced.

Thermo-imaging copy systems are also known, see for example U.S. Pat. No. 2,663,657, issued Dec. 22, 1953 to Carl S. Miller and Bryce L. Clark. For this use, microcapsules containing a solution of a cyclopolymethylenefluoran compound are prepared having capsule wall material which is ruptured by heating. Such microcapsules are admixed with acid electron-acceptor material in a matrix of a heat sensitive material such as a wax, and applied to a suitable paper substrate. Visible markings are produced when such a thermo-imaging paper is processed with an original to be copied in a thermo-imaging apparatus.

I claim:
1. A fluoran compound represented by the general formula

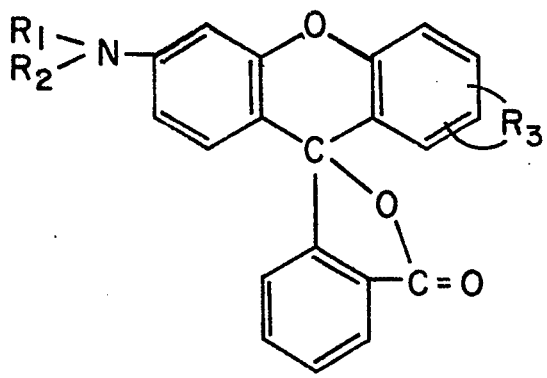

wherein $R_1$ and $R_2$ each represent a lower alkyl group containing one to four carbon atoms and wherein $R_3$ is a cyclopolymethylene group containing from three to four carbon atoms.

2. The compound of claim 1 wherein said fluoran compound is selected from the group consisting of 1,2-cyclotrimethylene-6-diethylamino fluoran and 2,3-cyclotrimethylene-6-diethylamino fluoran and mixtures thereof.

3. The compound of claim 1 wherein said fluoran compound is selected from the group consisting of 1,2-cyclotetramethylene-6-diethylamino fluoran and 2,3-cyclotetramethylene-6-diethylamino fluoran and mixtures thereof.

4. A pressure-sensitive transfer sheet comprising a substrate having coated thereon pressure rupturable microcapsules containing an organic solvent solution of the substantially colorless cyclopolymethylenefluoran compound of claim 1, said organic solvent solution of said substantially colorless cyclopolymethylenefluoran compounds being capable of forming a colored dye in contact with an electron-acceptor.

5. The pressure sensitive transfer sheet of claim 4 in which the substrate is paper.

6. A process for producing a cyclopolymethylenefluoran compound by reacting equimolar quantities of a 2-(4'-N,N lower alkyl substituted amino-2'hydroxybenzoyl) benzoic acid with a phenol selected from the group consisting of 5-indanol and 5,6,7,8-tetrahydro-1-naphthol for a time period ranging from about 1 to about 24 hours at a temperature ranging from about 35 to about 110° C. in sulfuric acid having a concentration above about 70% and thereafter recovering the reaction product.

* * * * *